US010492667B2

(12) United States Patent
Karaki et al.

(10) Patent No.: US 10,492,667 B2
(45) Date of Patent: Dec. 3, 2019

(54) OPTICAL FIBER SCANNING APPARATUS AND OPTICAL SCANNING TYPE ENDOSCOPE

(71) Applicant: OLYMPUS CORPORATION, Tokyo (JP)

(72) Inventors: Kazuhisa Karaki, Shiojiri (JP); Mamoru Hasegawa, Nagano (JP); Hiroya Fukuyama, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 432 days.

(21) Appl. No.: 15/341,058

(22) Filed: Nov. 2, 2016

(65) Prior Publication Data
US 2017/0049304 A1  Feb. 23, 2017

Related U.S. Application Data

(63) Continuation of application No. PCT/JP2015/058286, filed on Mar. 19, 2015.

(30) Foreign Application Priority Data

May 2, 2014 (JP) .................... 2014-095333

(51) Int. Cl.
A61B 1/00 (2006.01)
A61B 1/04 (2006.01)
A61B 1/06 (2006.01)

(52) U.S. Cl.
CPC ...... *A61B 1/00172* (2013.01); *A61B 1/00158* (2013.01); *A61B 1/00165* (2013.01);
(Continued)

(58) Field of Classification Search
CPC ..... A61B 1/07; A61B 1/00163; A61B 5/0062; A61B 5/0066; A61B 5/0068;
(Continued)

(56) References Cited

U.S. PATENT DOCUMENTS 4,924,857 A * 5/1990 Mahmoodian ..... A61B 17/0293
                                                                600/220
7,129,472 B1 * 10/2006 Okawa ............... A61B 1/00059
                                                                250/234
(Continued)

FOREIGN PATENT DOCUMENTS

EP      1142529 A1    10/2001
EP      1901107 A1     3/2008
(Continued)

OTHER PUBLICATIONS

International Search Report dated May 26, 2015 issued in PCT/JP2015/058286.

*Primary Examiner* — John P Leubecker
*Assistant Examiner* — Shankar Raj Ghimire
(74) *Attorney, Agent, or Firm* — Scully, Scott, Murphy & Presser, P.C.

(57) ABSTRACT

In an optical fiber scanning apparatus, an optical fiber to which a permanent magnet is disposed and which is configured to emit illumination light from a distal end portion is arranged in a hollow portion where a magnetic field generation unit is disposed of a frame body, the frame body for which a cross section of the hollow portion is a square includes a first frame body for which planar coils are disposed respectively on a first surface and a second surface that are orthogonal to each other, and a second frame body for which planar coils are disposed respectively on a third surface and a fourth surface that are orthogonal to each other, and which is bonded with the first frame body, and the first surface to the fourth surface configure inner surfaces of the hollow portion.

11 Claims, 10 Drawing Sheets

(52) U.S. Cl.
CPC .......... *A61B 1/00167* (2013.01); *A61B 1/042*
(2013.01); *A61B 1/0669* (2013.01)
(58) Field of Classification Search
CPC ............ A61B 1/00172; A61B 1/00165; A61B
1/00167; G02B 27/1033; G02B 26/103;
G02B 21/0036
USPC ........................................................ 600/182
See application file for complete search history.

(56) References Cited

U.S. PATENT DOCUMENTS

| | | | | |
|---|---|---|---|---|
| 7,267,229 | B2* | 9/2007 | Chen ...................... | B65D 19/06 206/386 |
| 2007/0236782 | A1* | 10/2007 | Sano .................. | A61B 1/00096 359/368 |
| 2008/0249369 | A1* | 10/2008 | Seibel ................. | A61B 1/0008 600/182 |
| 2009/0015894 | A1* | 1/2009 | Rosman ............... | A61B 5/0062 359/199.1 |
| 2010/0207015 | A1* | 8/2010 | Bierhoff ............... | A61B 5/0062 250/227.26 |
| 2010/0276063 | A1* | 11/2010 | Bui ..................... | H01J 49/4225 156/91 |
| 2011/0011855 | A1* | 1/2011 | Han ...................... | A47B 47/05 220/4.33 |
| 2014/0114131 | A1* | 4/2014 | Sakai ................. | G02B 21/0028 600/182 |
| 2015/0331233 | A1* | 11/2015 | Shimamoto .......... | G02B 26/103 385/6 |

FOREIGN PATENT DOCUMENTS

| | | | | |
|---|---|---|---|---|
| JP | 2001-174744 | A | | 6/2001 |
| JP | 2008-116922 | A | | 5/2008 |
| JP | 2014044265 | A | * | 3/2014 ......... A61B 1/00165 |
| JP | 2014-081484 | A | | 5/2014 |
| WO | WO 01/24686 | A1 | | 4/2001 |
| WO | WO 2014/061354 | A1 | | 4/2014 |
| WO | WO-2014061354 | A1 | * | 4/2014 ........... G02B 26/103 |

* cited by examiner

OPTICAL FIBER SCANNING APPARATUS AND OPTICAL SCANNING TYPE ENDOSCOPE

CROSS REFERENCE TO RELATED APPLICATION

This application is a continuation application of PCT/JP2015/058286 filed on Mar. 19, 2015 and claims benefit of Japanese Application No. 2014-095333 filed in Japan on May 2, 2014, the entire contents of which are incorporated herein by this reference.

BACKGROUND OF THE INVENTION

1. Field of the Invention

The present invention relates to an optical fiber scanning apparatus including a frame body to which a magnetic field generation unit is disposed, and an optical fiber which emits light from a distal end portion and on which a permanent magnet is disposed, and an optical scanning type endoscope including the optical fiber scanning apparatus at a distal end portion of an insertion portion.

2. Description of the Related Art

An image pickup apparatus using an image pickup device such as a CCD or a CMOS image sensor simultaneously receives reflected light from a subject by many photodetectors arranged in a matrix shape, and acquires an object image. In the case of an endoscope which photographs a dark inside of a body, an image in a range illuminated by light from a light source is acquired.

In contrast, in an optical scanning type image pickup apparatus, while an object is scan-irradiated by a light spot, the reflected light is successively received, and an object image is prepared based on the light reception data.

For example, in the optical scanning type image pickup apparatus, by an optical fiber scanning apparatus two-dimensionally scanning a distal end portion of an optical fiber that guides light from a light source, scan irradiation of the light spot is performed.

Further, in an endoscope, diameter reduction of a distal end portion is strongly demanded in order to reduce invasion. In order to reduce a diameter of an optical scanning type endoscope for which an optical fiber scanning apparatus is disposed at a distal end portion, the diameter reduction of the optical fiber scanning type image pickup apparatus is an important issue.

Japanese Patent Application Laid-Open Publication No. 2008-116922 discloses an optical fiber scanning apparatus using magnetic force. In the conventional optical fiber scanning apparatus, an optical fiber where a permanent magnet is disposed is arranged at a center of a magnetic field generation unit formed of four electromagnets (magnetic field generation portions) which are orthogonally arranged/oppositely arranged inside a cylinder.

In the optical fiber scanning apparatus, a coil of the electromagnet is a winding coil in which a copper wire is wound in an elliptic shape around an outer periphery of a magnetic core formed of a soft magnetic body.

SUMMARY OF THE INVENTION

An optical fiber scanning apparatus of an embodiment is an optical fiber scanning apparatus for which an optical fiber which is configured to emit illumination light from a distal end portion and to which a permanent magnet is disposed is arranged in a hollow portion where a magnetic field generation unit is disposed of a frame body, the frame body for which a cross section of the hollow portion is a square includes: a first frame body for which planar coils are disposed respectively on a first surface and a second surface that are orthogonal to each other; and a second frame body for which planar coils are disposed respectively on a third surface and a fourth surface that are orthogonal to each other, and which is bonded with the first frame body, and the first surface to the fourth surface configure inner surfaces of the hollow portion.

In addition, an optical scanning type endoscope of another embodiment has, at a distal end portion of an insertion portion, an optical fiber scanning apparatus for which an optical fiber which is configured to emit illumination light from a distal end portion and to which a permanent magnet is disposed is arranged in a hollow portion where a magnetic field generation unit is disposed of a frame body, wherein the frame body for which a cross section of the hollow portion is a square includes: a first frame body for which planar coils are disposed respectively on a first surface and a second surface that are orthogonal to each other; and a second frame body for which planar coils are disposed respectively on a third surface and a fourth surface that are orthogonal to each other, and which is bonded with the first frame body, and the first surface to the fourth surface configure inner surfaces of the hollow portion.

DETAILED DESCRIPTION OF THE PREFERRED EMBODIMENTS

First Embodiment

Figure 1:
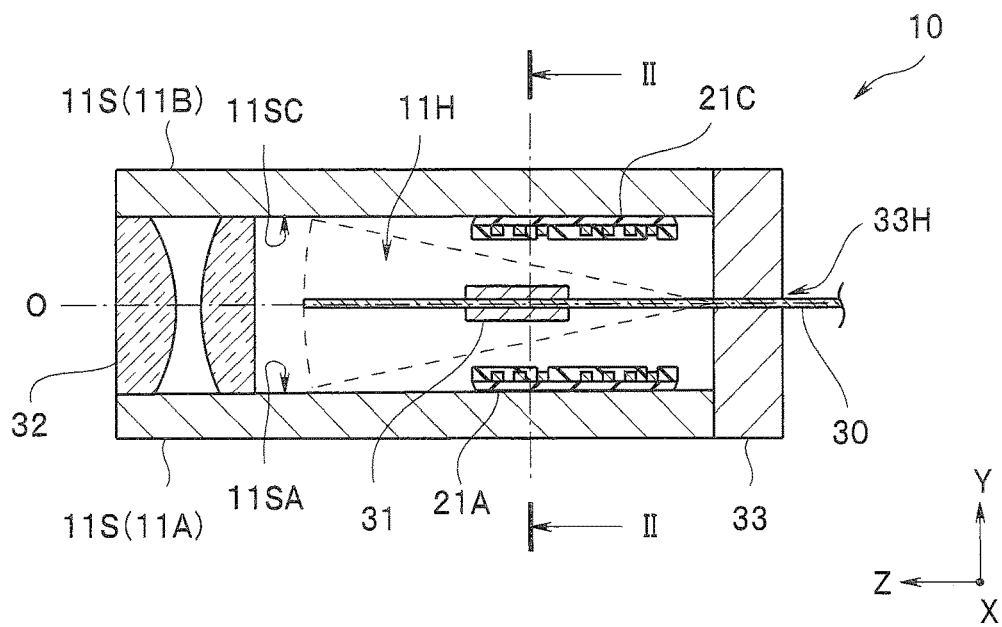
FIG. 1 is a sectional view along a center line of an optical fiber scanning apparatus in a first embodiment.
Figure 2:
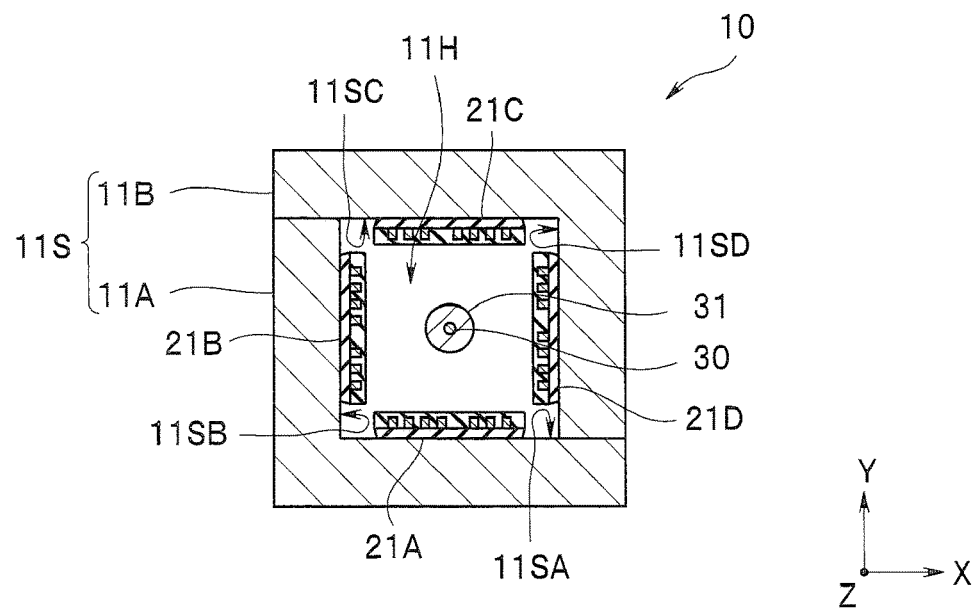
FIG. 2 is a sectional view along a II-II line in FIG. 1 of the optical fiber scanning apparatus in the first embodiment.

Using FIG. 1 to FIG. 3, an optical fiber scanning apparatus 10 in the first embodiment will be described. Note that, in a following description, drawings based on respective embodiments are schematic, it is to be taken into consideration that relations between thicknesses and widths of respective portions and ratios of the thicknesses of the respective portions or the like are different from actual ones, and portions where mutual dimensional relations or ratios are different are sometimes included among the drawings.

The optical fiber scanning apparatus 10 has a frame body 11S with a hollow portion 11H, one part of which is an opening, an optical fiber 30 arranged along a center line O in a long axis direction (Z direction) of the hollow portion 11H of the frame body 11S, a magnetic field generation unit 21U provided with four coil chips 21A to 21D, and an illumination optical system 32.

The optical fiber 30 guides light from a light source unit (see FIG. 17) and emits illumination light from a distal end portion. The illumination light spot-irradiates an object through the illumination optical system 32 formed of a plurality of lenses. Note that the illumination optical system 32 is not an essential component.

To a rear portion of the distal end portion of the optical fiber 30, a permanent magnet 31 is bonded by an adhesive or the like. For example, the permanent magnet 31 formed of an SmCo alloy is a cylindrical type and is magnetized in a longitudinal direction. The optical fiber 30 is inserted through a through-hole 33H of a holding member 33, and is bonded to the holding member 33. The distal end portion of the optical fiber 30 to which a bond portion (proximal end portion) of the holding member 33 is fixed is movable within an XY plane vertically and horizontally with the proximal end portion as a base point.

The frame body 11S has the hollow portion 11H, a cross section (an XY plane) of which orthogonal to the center line O is a square. The frame body 11S is provided with a first frame body 11A, and a second frame body 11B bonded with the first frame body 11A. For bonding, an adhesive may be used or fastening may be performed using a screw.

It is preferable that the frame body 11S, that is, the first frame body 11A and second frame body 11B, is formed of a metal for accurate processing, and it is especially preferable that the frame body 11S is formed of stainless steel or an aluminum alloy which is excellent in machinability and weather resistance. In addition, from a viewpoint of magnetic flux leakage reduction or the like, it is also especially preferable that the frame body 11S is formed of a soft magnetic material of high magnetic permeability such as permalloy.

A housing 11S is a positioning member for accurately disposing the magnetic field generation unit 21U. Therefore, it is not a problem even when a thickness of the wall is thin as long as the wall has measurable strength. While the thickness of the wall of the housing 11S is illustrated thick in FIG. 2 or the like, the thickness is, for example, equal to or larger than 10 μm and equal to or smaller than 100 μm. When the thickness is equal to or smaller than the range, miniaturization (diameter reduction) is easy. In addition, the housing 11S may be a substantially rectangular parallelepiped for which corner portions of an outer surface are processed into curved surfaces or chamfered.

On an inner side of the first frame body 11A, a first surface 11SA and a second surface 11SB orthogonal to the first surface 11SA are provided. On an inner side of the second frame body 11B, a third surface 11SC and a fourth surface 11SD orthogonal to the third surface 11SC are provided. Then, when a first frame body 11A and a second frame body are bonded, the first surface 11SA to the fourth surface 11SD configure inner surfaces of the hollow portion 11H of the frame body 11S.

All corner portions of a cross section of the hollow portion 11H formed by bonding the second surface 11SB and the third surface 11 SC so as to be orthogonal and the first surface 11SA and the fourth surface 11SD so as to be orthogonal are 90 degrees. In addition, a shape of the first frame body 11A and a shape of the second frame body 11B are set such that lengths of four sides of the cross section of the hollow portion 11H to be formed become equal when bonding is performed.

In the hollow portion 11H of the frame body 11S, the magnetic field generation unit 21U is disposed. That is, the coil chip 21A is disposed on the first surface 11SA of the first frame body 11A, and the coil chip 21B is disposed on the second surface 11SB. The coil chip 21C is disposed on the third surface 11SC of the second frame body 11B, and the coil chip 21D is disposed on the fourth surface 11SD. Note that, hereinafter, each of the coil chips 21A to 21D is referred to as a coil chip 21.

The coil chip 21 is bonded to the frame body 11S by fastening with a screw or an adhesive, for example. For positioning during bonding, for example, a recessed portion to which the coil chip 21A is to be fitted may be provided on the first surface 11 SA, an L-shaped projected portion to which a side face of the coil chip 21A is to be in contact may be provided, or a positioning jig to which the side face of the coil chip 21A is to be in contact may be used during bonding.

Figure 3:
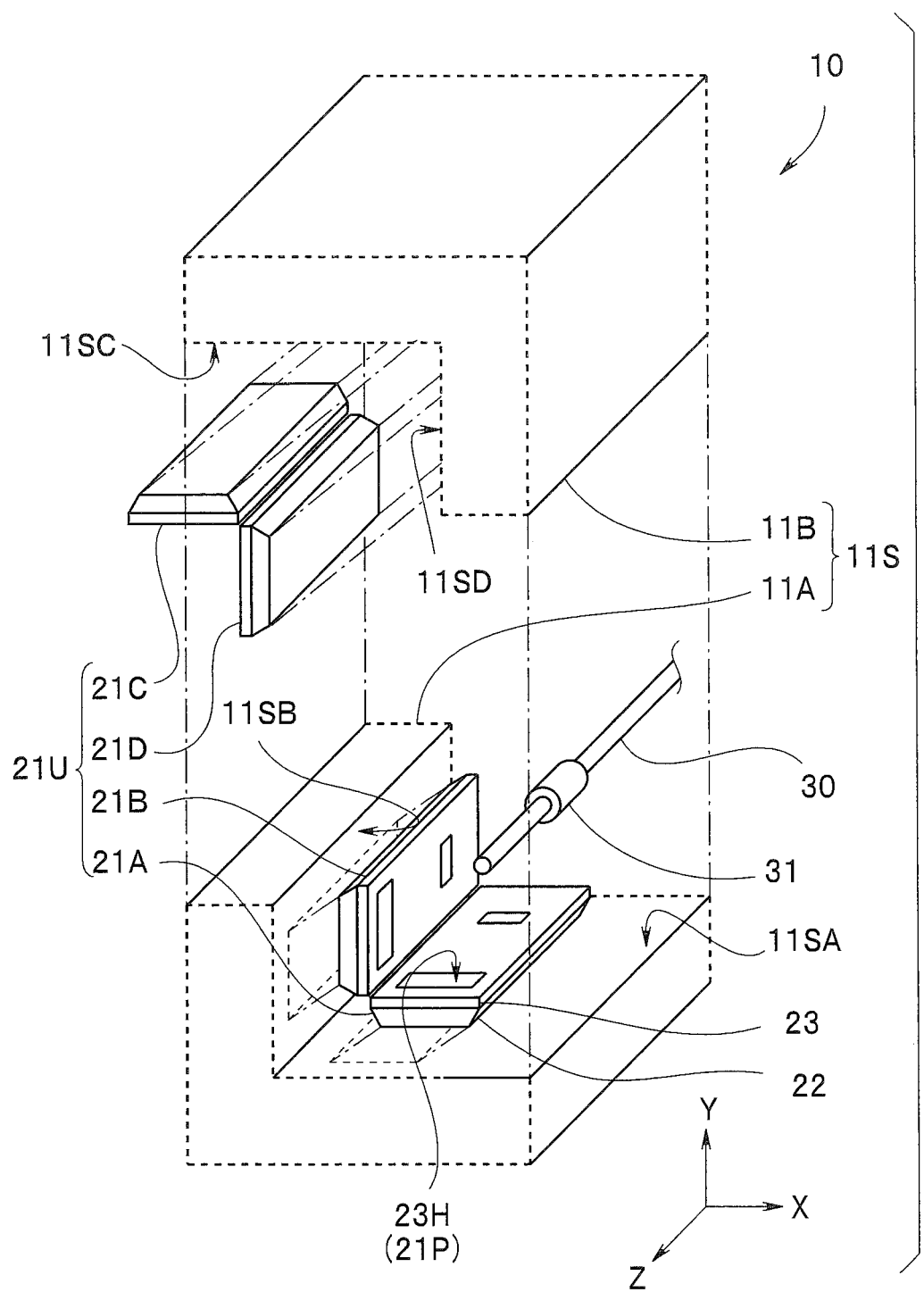
FIG. 3 is an exploded view of a main section of the optical fiber scanning apparatus in the first embodiment.
Figure 4:
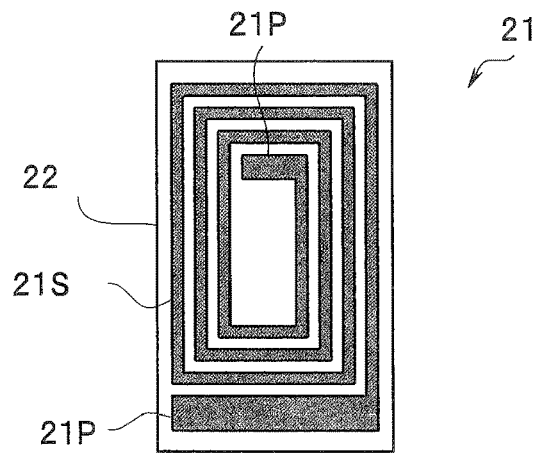
FIG. 4 is a top view of a planar coil of the optical fiber scanning apparatus in the first embodiment.

As illustrated in FIG. 3 and FIG. 4 or the like, for the coil chip 21, to a base body 22 formed of silicon, a planar coil 21S which is a drive coil in a spiral shape is disposed through an insulating layer of a silicon oxide or the like (not shown in the figure). The planar coil 21S is covered with an insulating layer 23 formed of a resin such as polyimide or epoxy except for contact hole portions at an upper part of a bond pad 21P at both ends. The illustrated planar coil 21S includes a conductor layer (planar coil) formed of a patterned low resistance metal such as copper or gold and an insulating layer covering the conductor layer. Note that, while a bond pad is arranged also at a coil center in the coil chip 21, in order to provide the bond pad around the coil, one insulating layer/lead-out wiring may be provided further, or the coil chip 21 may be a multilayer coil in which a plurality of coils are laminated through the insulating layer.

The coil chip 21 can be manufactured by disposing many planar coils on a silicon wafer and then dividing the planar coils by a MEMS semiconductor process. For example, by using a highly accurate resist mask manufactured by a photolithographic method using photoresist and a photomask and performing patterning by an additive method, a subtraction method or the like, the coil chip 21 including the planar coil 21S with high accuracy can be easily manufactured in large quantities.

Note that, in the optical fiber scanning apparatus 10, the first frame body 11A and the second frame body 11B are in substantially the same shape. In addition, the coil chips 21A to 21D are in the same configuration. Therefore, for the optical fiber scanning apparatus 10, the first frame body 11A and the second frame body 11B can be manufactured in the same process, the coil chips 21A to 21D can be manufactured in the same process, and further, the first frame body 11A to which the coil chips 21A and 21B are disposed and the second frame body 11B to which the coil chips 21C and 21D are disposed can be manufactured in the same process. Therefore, the optical fiber scanning apparatus 10 is easy to manufacture.

The two bond pads 21P are connected with a power source unit (see FIG. 17 or the like) which supplies a driving current by wiring not shown in the figure. The planar coil 21S generates a magnetic field in a direction orthogonal to a main surface of the coil chip 21 when the driving current is applied to the bond pad 21P. Strength of the magnetic field is set by a current value of the driving current and a number of turns of a spiral coil or the like. When a direction of the driving current flowing through the coil is inverted, the direction of the generated magnetic field is inverted.

In the optical fiber scanning apparatus 10, planar coils 21S1 and 21S2 are disposed respectively on the first surface 11SA and the second surface 11SB that are orthogonal of the first frame body 11A, and planar coils 21S3 and 21S4 are disposed respectively on the third surface 11SC and the fourth surface 11SD that are orthogonal of the second frame body 11B. That is, the planar coil 21S1 and the planar coil 21S3 are arranged at opposite positions, and the planar coil 21S2 and the planar coil 21S4 are arranged at opposite positions.

Therefore, the planar coils 21S1 and 21S3 generate the magnetic field in a Y axis direction, and the planar coils 21S2 and 21S4 generate the magnetic field in an X axis direction. The optical fiber 30 (permanent magnet 31) is arranged at equal distances from the four planar coils 21S1 to 21S4, that is, at a center of the hollow portion 11H of the frame body 11S.

Next, a driving method of the optical fiber scanning apparatus 10 will be simply described.

Figure 5A:
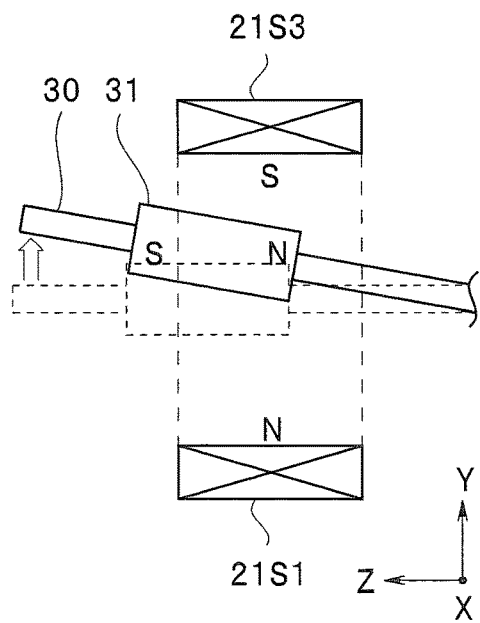
FIG. 5A is a sectional schematic diagram for explaining a driving method of the optical fiber scanning apparatus in the first embodiment.

As illustrated in FIG. 5A, when the driving current is supplied to the planar coil 21S1, for example, the magnetic field in which an inner surface side is an N pole is generated. Simultaneously, when the driving current is supplied to the planar coil 21S3, for example, the magnetic field in which the inner surface side is an S pole is generated. That is, the planar coil 21S1 and the planar coil 21S3 that are oppositely arranged generate the magnetic fields of the different magnetic poles on the inner surface side.

Therefore, a rear end side (N pole) of the permanent magnet 31 arranged within the magnetic field is pulled up in a Y axis upper direction. Therefore, a distal end of the optical fiber 30 is also moved in the Y axis upper direction.

Figure 5B:
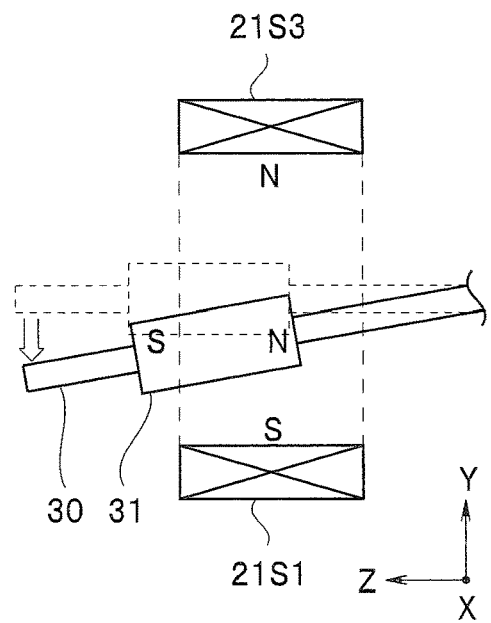
FIG. 5B is a sectional schematic diagram for explaining the driving method of the optical fiber scanning apparatus in the first embodiment.

On the other hand, as illustrated in FIG. 5B, when the driving current in the direction opposite to that in the case of FIG. 5A is supplied to the planar coil 21S1, the magnetic field in which the inner surface side is the S pole is generated. Similarly, when the driving current in the direction opposite to that in the case of FIG. 5A is supplied to the planar coil 21S3, the magnetic field in which the inner surface side is the N pole is generated. Then, the rear end side (N pole) of the permanent magnet 31 arranged within the magnetic field is pulled down in a Y axis lower direction. Therefore, the distal end portion of the optical fiber 30 is also moved in the Y axis lower direction.

By controlling the direction of the driving current supplied to the planar coils 21S1 and 21S3, the distal end portion of the optical fiber 30 is scanned in the Y axis direction. Similarly, by controlling the direction of the driving current supplied to the planar coils 21S2 and 21S4, the distal end portion of the optical fiber 30 is scanned in the X axis direction.

Note that the permanent magnet 31, the optical fiber or the magnetic field generation unit 21U may be arranged such that the magnetic field is applied to a distal end side of the permanent magnet 31. In addition, for example, scanning is possible even when only the planar coil 21S1 and the planar coil 21S2 are driven.

By controlling the direction of the driving current supplied to the four planar coils 21S1 to 21S4, the distal end portion of the optical fiber 30 is two-dimensionally scanned within the XY plane. A scanning width is controlled by a driving current value. As a result, a light spot emitted from the distal end portion of the optical fiber 30 is two-dimensionally scanned.

Figure 6A:
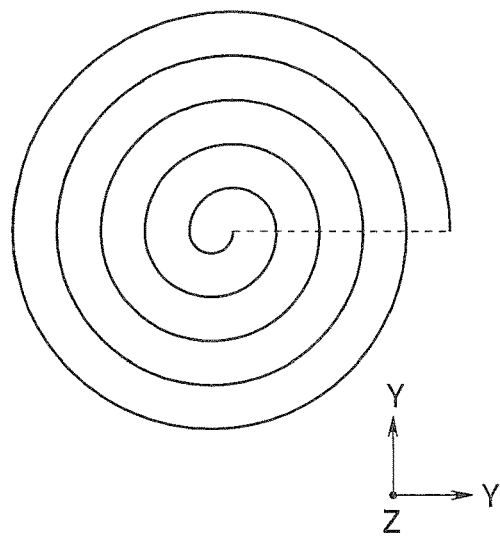
FIG. 6A is a diagram for explaining a scanning method of the optical fiber scanning apparatus in the first embodiment.
Figure 6B:
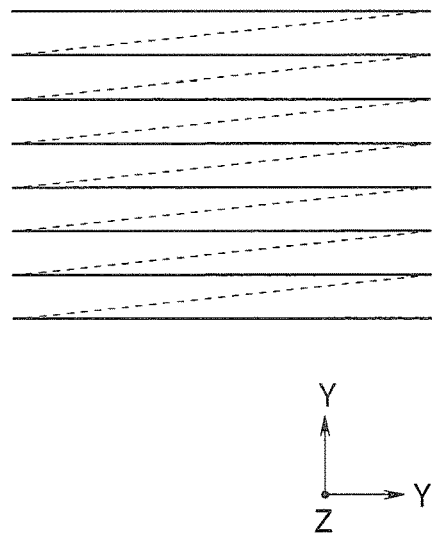
FIG. 6B is a diagram for explaining the scanning method of the optical fiber scanning apparatus in the first embodiment.

As a two-dimensional scanning system, a spiral scanning system illustrated in FIG. 6A or a raster scanning system illustrated in FIG. 6B is preferable since image processing is easy, and the raster scanning system is especially preferable since illumination can be uniformly performed.

Then, the optical fiber scanning apparatus 10 has a small diameter since the magnetic field generation unit 21U is formed of extremely thin coil chips 21A to 21D, a thickness of which is equal to or larger than 10 μm and is equal to or smaller than 200 μm for example, because the planar coil 21S is provided. Further, since the coil chips 21A to 21D are respectively disposed on the inner surfaces of the hollow portion 11H of the square cross section of the frame body 11S, the coil chips 21A to 21D are accurately arranged.

Therefore, the optical fiber scanning apparatus 10 has the small diameter and is capable of performing highly accurate scan irradiation.

MODIFICATIONS

Next, optical fiber scanning apparatuses 10A to 10H in modifications of the first embodiment will be described. Since the optical fiber scanning apparatuses 10A to 10H are similar to the optical fiber scanning apparatus 10, same signs are attached to components of the same functions and descriptions are omitted. Note that, in the following diagrams, the optical fiber and the magnetic field generation unit or the like are sometimes not illustrated.

The optical fiber scanning apparatuses 10A to 10I1 have effects of the optical fiber scanning apparatus 10 and have further characteristic effects.

Modification 1

Figure 7:
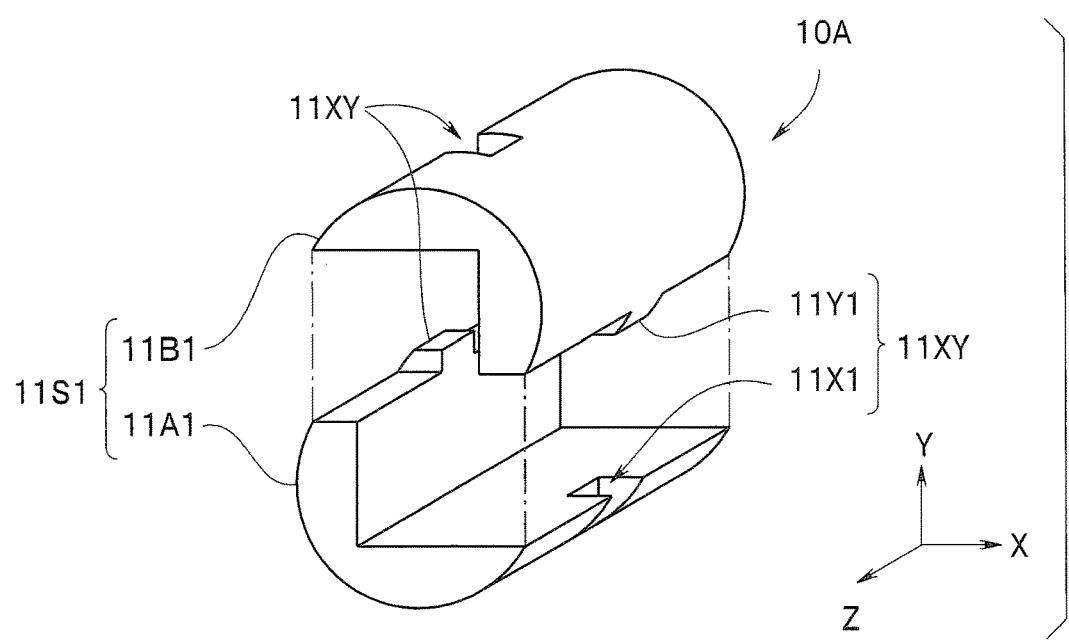
FIG. 7 is an exploded view of the main section of the optical fiber scanning apparatus in a modification 1.

As illustrated in FIG. 7, the optical fiber scanning apparatus 10A in the modification 1 is provided with a frame body 11S1 with a hollow portion of a square cross section, for which a first frame body 11A1 and a second frame body 11B1 are bonded, similarly to the optical fiber scanning apparatus 10. While the outer surface of the frame body 11S is a rectangular parallelepiped, the outer surface of the frame body 11S1 is columnar. Therefore, the optical fiber scanning apparatus 10A has a diameter smaller than that of the optical fiber scanning apparatus 10.

Note that an outer surface shape of the frame body may be a substantially rectangular parallelepiped, substantially columnar with a groove portion or the like on the outer surface, a polygonal prism shape, or a truncated conical shape or the like.

Further, in the optical fiber scanning apparatus 10A, at a bond portion of the first frame body 11A1 and the second frame body 11B1, two sets of fitting portions 11XY are provided. That is, by fitting a projected portion 11X1 of the first frame body 11A1 and a recessed portion 11Y1 of the second frame body 11B1, and a recessed portion 11X2 of the first frame body 11A1 and a projected portion 11Y2 of the second frame body 11B1, a positional relation between the first frame body 11A1 and the second frame body 11B1 is uniquely defined. Note that at least one set of the fitting portions 11XY with two or more contact surfaces is sufficient. Further, a shape of the projected portion may be columnar or the polygonal prism or the like as long as the recessed portion is fitted.

Therefore, the first frame body 11A1 and the second frame body 11B1 can be more easily and accurately bonded in the optical fiber scanning apparatus 10A than in the optical fiber scanning apparatus 10.

Note that it is needless to say that the optical fiber scanning apparatus for which the outer surface of the frame body 11S1 is columnar and the fitting portion is not provided and the optical fiber scanning apparatus for which the outer surface of the frame body 11S1 is not columnar but the fitting portion is provided have respective effects.

Modification 2

Figure 8A:
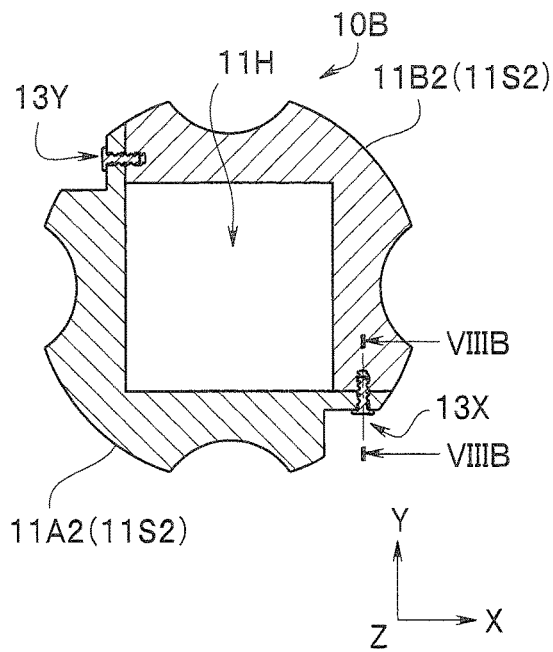
FIG. 8A is a sectional view of the main section of the optical fiber scanning apparatus in a modification 2.
Figure 8B:
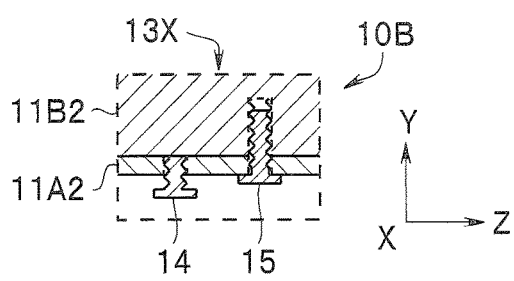
FIG. 8B is a sectional view along a VIIIB-VIIIB line in FIG. 8A of the optical fiber scanning apparatus in the modification 2.
Figure 8C:
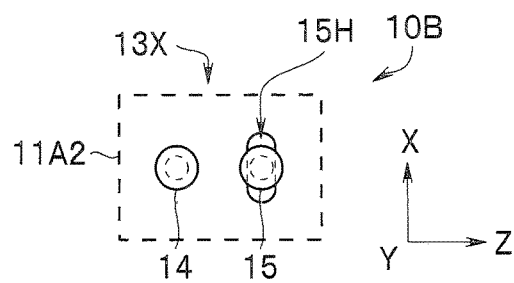
FIG. 8C is a top view of the main section of the optical fiber scanning apparatus in the modification 2.

As illustrated in FIG. 8A to FIG. 8C, a frame body 11S2 of the optical fiber scanning apparatus 10B in the modification 2 includes adjustment portions 13X and 13Y configured to finely adjust the positional relation between the first frame body 11A2 and second frame body 11B2. The adjustment portion 13X is the adjustment portion for performing fine adjustment in the Y axis direction and fixation of an X axis, and the adjustment portion 13Y is the adjustment portion for performing the fine adjustment in the X axis direction and fixation of a Y axis.

Note that FIG. 8B is a sectional view along a VIIIB-VIIIB line in FIG. 8A, and FIG. 8C is a plan view when viewing FIG. 8B from the Y axis direction.

As illustrated in FIG. 8B and FIG. 8C, at the adjustment portion 13X, the first frame body 11A2 has a screw hole to engage with an adjustment screw 14. On the other hand, a fixing screw 15 is inserted through an oblong hole 15H with an adjustment margin in the X axis direction. The second frame body 11B2 has a screw hole to engage with the fixing screw 15 and a contact surface with which a distal end of the adjustment screw 14 is in contact.

The fixing screw 15 fixed to the second frame body 11B2 is in a movable state in the X axis direction inside the oblong hole 15H for which the X axis direction is a long axis direction. That is, for the first frame body 11A2 and the second frame body 11B2, since the adjustment portion 13X is provided, relative positions in the X axis direction are in a variable state. By a tightening state of the adjustment screw 14, the positional relation in the Y axis direction between the first frame body 11A2 and the second frame body 11B2 is adjusted, and is fixed by fastening the fixing screw 15.

Similarly, for the first frame body 11A2 and the second frame body 11B2, by the adjustment portion 13Y, the relative positions in the X axis direction can be finely adjusted.

In the optical fiber scanning apparatus 10B, while the magnetic field is generated by the magnetic field generation unit 21U, for example, while the magnetic field is actually measured by a gauss meter or a scanning situation of an illumination light spot is confirmed, by finely adjusting positions in the X axis direction and the Y axis direction between the first frame body 11A2 and second frame body 11B2, the first frame body 11A2 and second frame body 11B2 can be fixed in the optimum positional relation.

Instead of the adjustment screw and the fixing screw in the adjustment portions 13X and 13Y, a leaf spring or a shim or the like may be used. In addition, an adjustment portion that finely adjusts a Z axis direction may be provided.

Note that, in the optical fiber scanning apparatus 10B, the first frame body 11A2 and the second frame body 11B2 are not in the same shape. In addition, an outer shape of the frame body 11S2 is substantially columnar with a groove. The substantially columnar frame body 11S2 has effects similar to that of the columnar frame body 11S.

Modification 3

Figure 9:
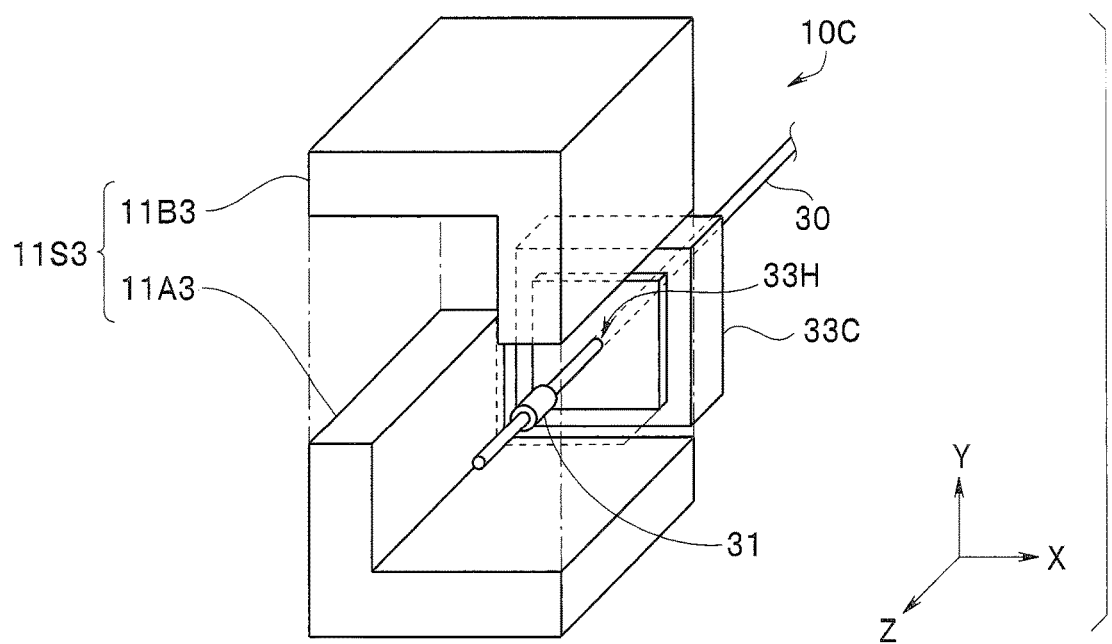
FIG. 9 is an exploded view of the main section of the optical fiber scanning apparatus in a modification 3.

As illustrated in FIG. 9, in the optical fiber scanning apparatus 10C in the modification 3, an optical fiber holding member 33C is fitted to a rear end portion of the hollow portion 11H of a frame body 11S3 formed of a first frame body 11A3 and a second frame body 11B3. To the optical fiber holding member 33C, the optical fiber 30 is inserted and fixed.

A position of the through-hole 33H of the optical fiber holding member 33C is at the center of the hollow portion of the square cross section formed when the first frame body 11A3 and the second frame body 11B3 are bonded.

In the optical fiber scanning apparatus 10C, it is easy to accurately arrange the optical fiber 30 along a center line of the hollow portion of the frame body 11S3.

Modification 4

Figure 10:
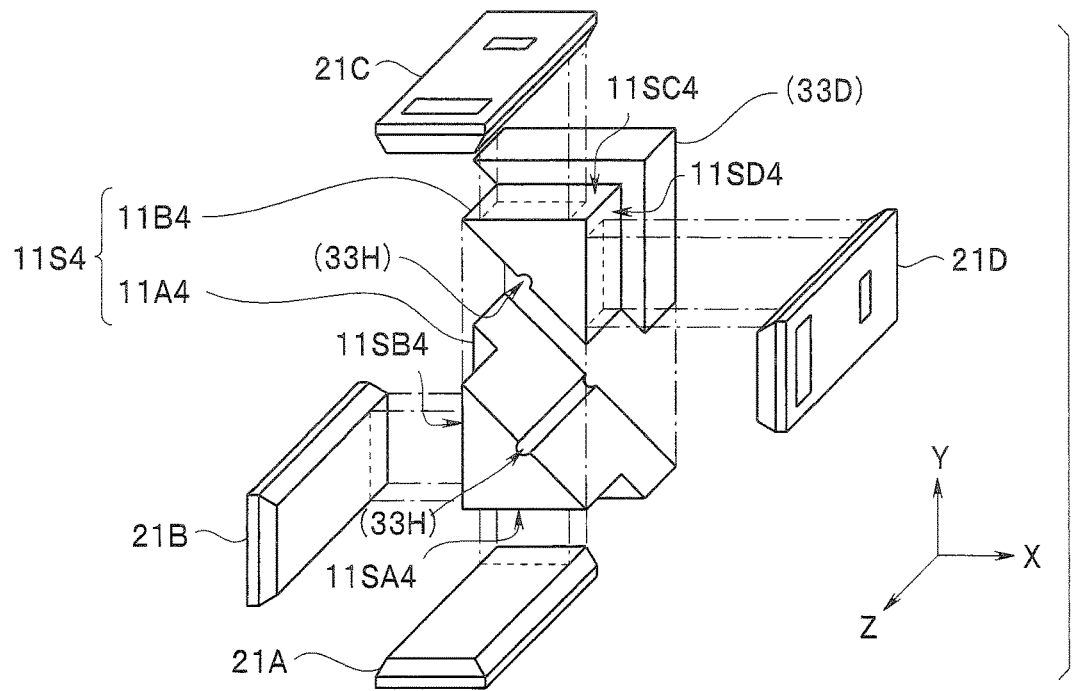
FIG. 10 is an exploded view of the main section of the optical fiber scanning apparatus in a modification 4.

As illustrated in FIG. 10, the optical fiber scanning apparatus 10D in the modification 4 has a frame body 11S4 for which the first frame body 11A4 and the second frame body 11B4 are bonded. On the rear end side of the frame body 11S4, an optical fiber holding member 33D with the through-hole 33H to which the optical fiber is inserted and fixed is extended integrally with the frame body 11S4.

Then, to four wall surfaces, 11SA4, 11SB4, 11SC4 and 11SD4, of a chip fixing portion of a square cross section on a distal end side of the frame body 11S4, a part of the coil chips 21A, 21B, 21C and 21D is bonded respectively.

Note that, though not shown in the figure, an outer peripheral portion of the optical fiber scanning apparatus 10D may be molded with a resin.

Modification 5

Figure 11:
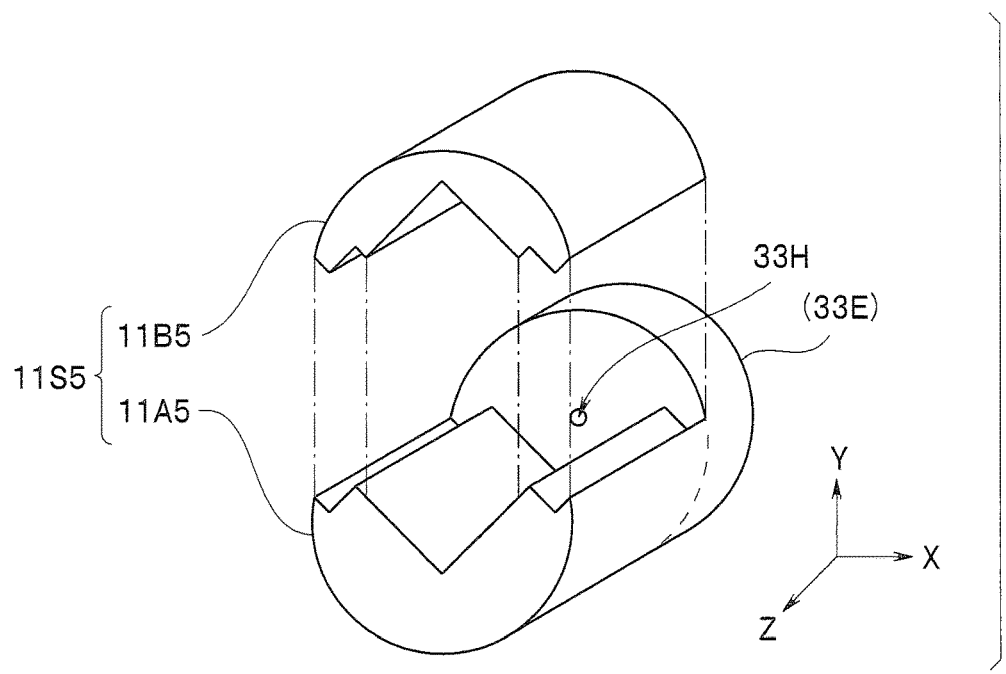
FIG. 11 is an exploded view of the main section of the optical fiber scanning apparatus in a modification 5.

As illustrated in FIG. 11, in the optical fiber scanning apparatus 10E in the modification 5, the outer surface of the frame body 11S5 is columnar similarly to the optical fiber scanning apparatus 10A. Therefore, the optical fiber scanning apparatus 10E has the diameter smaller than that of the optical fiber scanning apparatus 10.

Note that the shape of the first frame body 11A5 and the shape of the second frame body 11B5 are different.

In addition, the first frame body 11A5 and the second frame body 11B5 are bonded in the state of being in contact on a plurality of contact surfaces that are the positioning portion. Therefore, the positional relation between the first frame body 11A5 and the second frame body 11B5 is uniquely defined. The first frame body 11A5 and the second frame body 11B5 can be easily and accurately bonded in the optical fiber scanning apparatus 10E than in the optical fiber scanning apparatus 10. Note that, in order to define the positional relation between the first frame body 11A5 and the second frame body 11B5, both need to be in contact on at least two contact surfaces.

Further, in the optical fiber scanning apparatus 10E, on the rear end portion of the first frame body 11A5, a holding member 33E integrated with the first frame body 11A5 is extended. The position of the through-hole 33H is at the center of the hollow portion 11H formed when the first frame body 11A5 and the second frame body 11B5 are bonded.

In the optical fiber scanning apparatus 10E, it is easy to accurately arrange the optical fiber 30 along a center line of the hollow portion of the frame body 11S5.

Modification 6

Figure 12A:
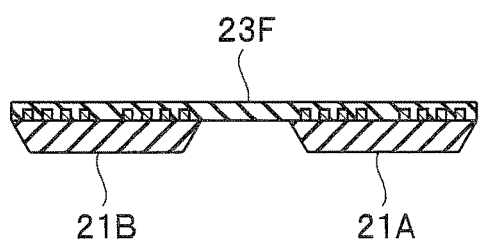
FIG. 12A is a sectional view of the planar coil of the optical fiber scanning apparatus in a modification 6.

As illustrated in FIG. 12A, in the optical fiber scanning apparatus 10F in the modification 6, the two coil chips 21A and 21B disposed to the first frame body 11A are connected by a flexible resin covering the two planar coils 21S1 and 21S2, for example, an insulating layer 23F formed of polyimide. In addition, though not shown in the figure, the two coil chips disposed to the second frame body 11B are also connected by the insulating layer covering the two planar coils.

Figure 12B:
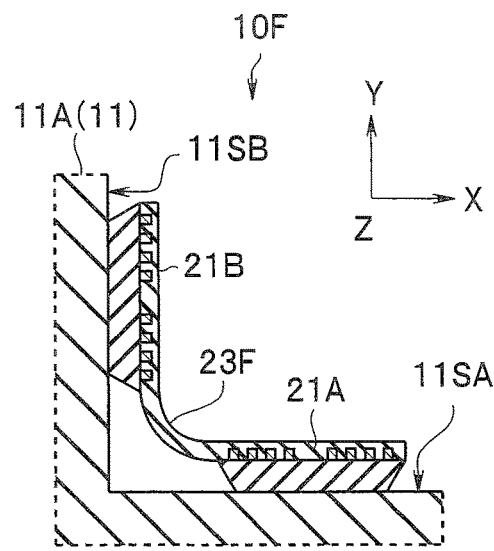
FIG. 12B is a sectional view of the main section of the optical fiber scanning apparatus in the modification 6.

In the optical fiber scanning apparatus 10F, the positional relation of the two coil chips 21 is defined before the coil chips 21 are disposed to the first frame body 11A or the like. Therefore, as illustrated in FIG. 12B, it is easier to accurately arrange the two planar coils 21S (coil chips 21) at the frame body 11S.

Modification 7

Figure 13A:
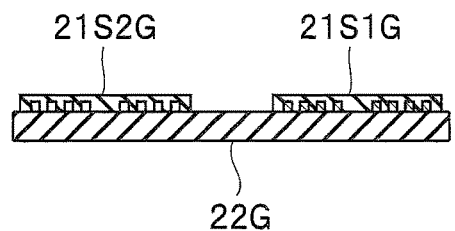
FIG. 13A is a sectional view of the planar coil of the optical fiber scanning apparatus in a modification 7.

As illustrated in FIG. 13A, in the optical fiber scanning apparatus 10G in the modification 7, two planar coils 21S1G and 21S2G disposed to the first frame body 11A are disposed to the base body 22G formed of one sheet of flexible resin. In addition, though not shown in the figure, the two planar coils disposed to the second frame body 11B are also disposed to the base body formed of one sheet of the flexible resin. It is preferable that the base body 22G and the insulating layer 23 covering the planar coils 21S are formed of the same polyimide for simplification of a manufacture process.

Figure 13B:
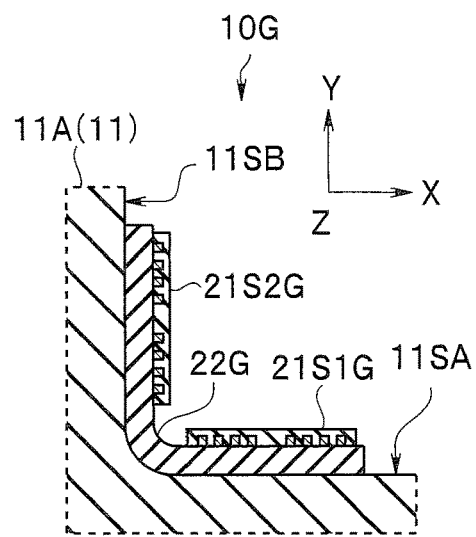
FIG. 13B is a sectional view of the main section of the optical fiber scanning apparatus in the modification 7.

In the optical fiber scanning apparatus 10G, the positional relation of the two coil chips 21 is defined before the coil chips 21 are disposed to the first frame body 11A or the like. Therefore, as illustrated in FIG. 13B, it is easier to accurately arrange the two planar coils 21S at the frame body 11S. Further, for the planar coils 21S, since a plurality of members can be simultaneously manufactured in a wiring formation process of a flexible wiring board, the optical fiber scanning apparatus 10G is easy to manufacture.

Modification 8

Figure 14:
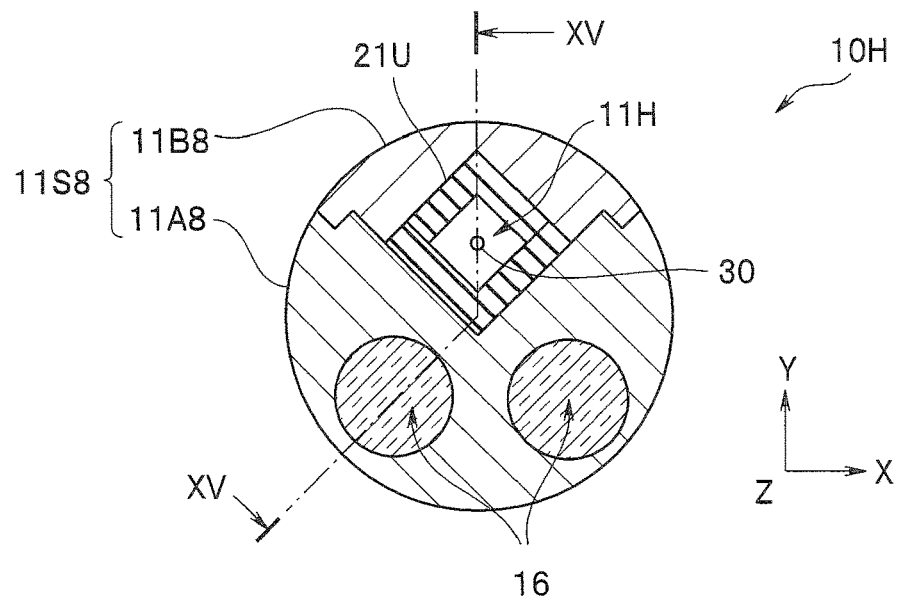
FIG. 14 is a sectional view in a long axis orthogonal direction of the optical fiber scanning apparatus in a modification 8.
Figure 15:
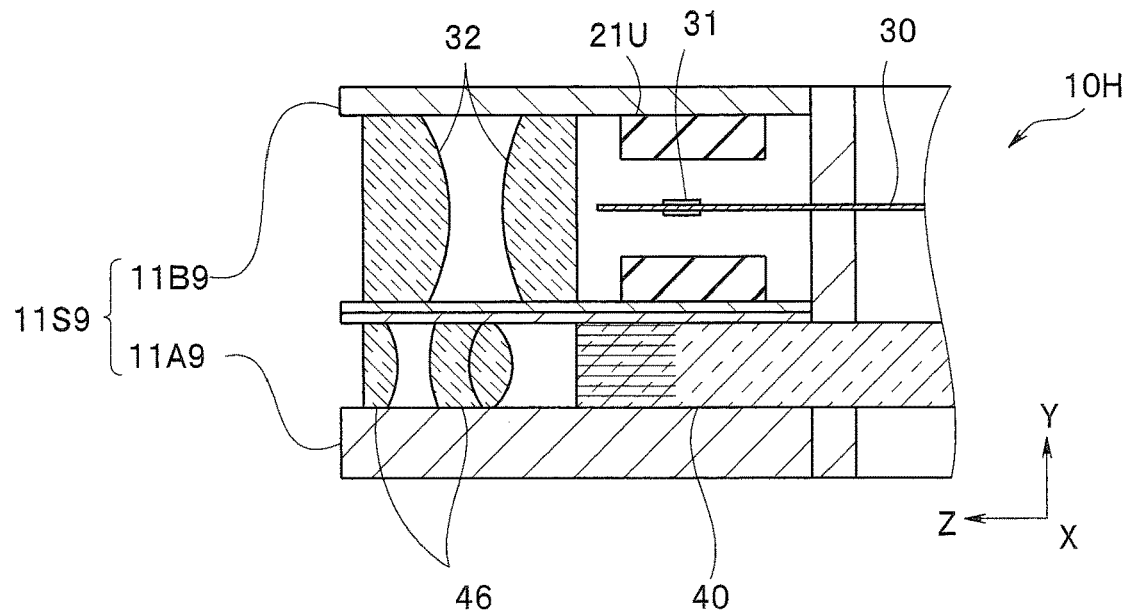
FIG. 15 is a sectional view along an XV-XV line in FIG. 14 of the optical fiber scanning apparatus in a modification 9.

As illustrated in FIG. 14 and FIG. 15, while the optical fiber scanning apparatus 10H in the modification 8 is similar to the already-described optical fiber scanning apparatus 10E (see FIG. 11), two incidence portions 16 of a detection unit 76 (see FIG. 17) which detects reflected light of light with which an object is irradiated from the optical fiber 30 are arranged in a frame body 11S8.

Note that FIG. 14 is a sectional view in a long axis orthogonal direction of the optical fiber scanning apparatus 10H, and FIG. 15 is a sectional view along an XV-XV line in FIG. 14.

As illustrated in FIG. 15, the incidence portion 16 is a distal end portion of an optical fiber (also referred to as "detection fiber", hereinafter) 40 which guides the reflected light. The reflected light made incident from the distal end portion of the optical fiber 40 through a detection optical system 46 formed of a plurality of lenses is guided to a main body device 3 (see FIG. 16 and FIG. 17). Note that it is preferable that the optical fiber 40 is a fiber bundle formed of a plurality of optical fibers. In addition, there may be one incidence portion 16 or three or more incidence portions 16.

Here, the optical fiber 40 is considered as a part of the detection unit 76. In addition, a photodiode (PD) element or the like which detects the reflected light may be directly arranged in the frame body 11S8 as the incidence portion 16.

For the optical fiber scanning apparatus 10H, since the incidence portions 16 of the detection unit 76 are arranged in the frame body 11S8, a structure is simple as a whole and the diameter is small compared to the optical fiber scanning apparatus in which the incidence portion 16 is disposed to a different member.

Note that, also in the optical fiber scanning apparatuses 10, 10A to 10C, 10E, 10F and 10G, by arranging the incidence portion 16 of the detection unit 76 in the frame body, the same effects as that of the optical fiber scanning apparatus 10H are provided.

Second Embodiment

Figure 16:
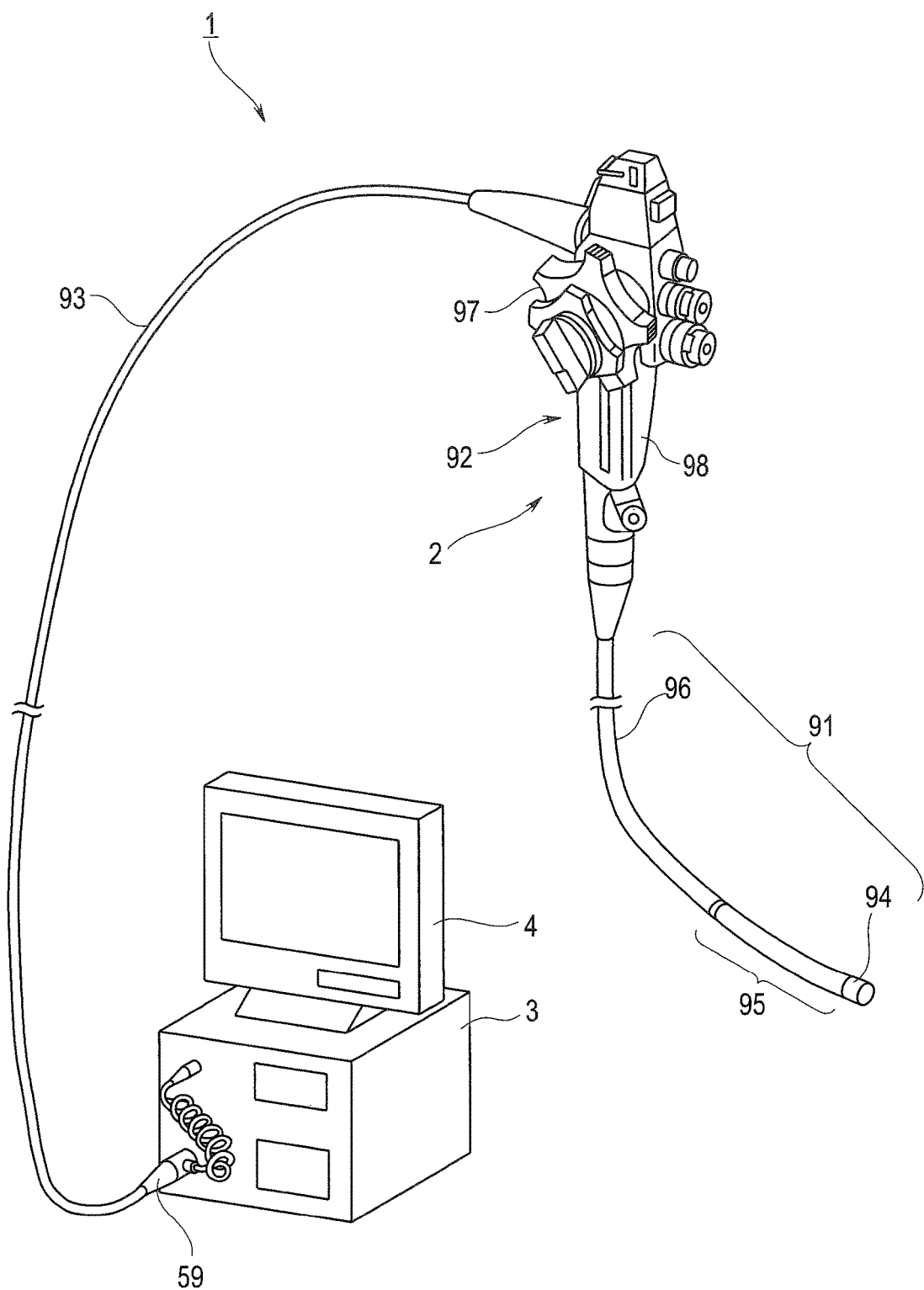
FIG. 16 is a perspective view of an endoscope system including an endoscope in a second embodiment.

An optical scanning type endoscope (referred to as "endoscope" hereinafter) 2 in the second embodiment illustrated in FIG. 16 has one of the already-described optical fiber scanning apparatuses 10 and 10A to 10H at a distal end portion 94 of an insertion portion 91. Hereinafter, the description will be given with the endoscope 2 including the optical fiber scanning apparatus 10 as an example.

An optical scanning type endoscope system (referred to as "endoscope system" hereinafter) 1 including the endoscope 2 is provided with the endoscope 2, the main body device 3 having functions of a light source device and a video processor, and a monitor 4. The endoscope 2 irradiates a subject with the illumination light while performing two-dimensional scanning by the optical fiber scanning apparatus 10, detects the reflected light (return light) from the subject, performs data processing in the main body device 3, and displays a generated subject image on the monitor 4.

The endoscope 2 is provided with an elongated insertion portion 91 to be inserted into a living body, an operation portion 92, and a universal cable 93 to which an electric cable or the like is inserted. The insertion portion 91 of the endoscope 2 includes the distal end portion 94, a bending portion 95, and a flexible tube portion 96. Note that, while the endoscope 2 of the embodiment is a so-called flexible endoscope, even a so-called rigid endoscope in which the insertion portion 91 is rigid has the effects described later.

To the operation portion 92, a bending operation knob 97 for performing a bending operation of the bending portion 95 is freely turnably disposed. A connection portion of the insertion portion 91 and the operation portion 92 is a grasping portion 98 to be grasped by a user.

The universal cable 93 extended from the operation portion 92 is connected with the main body device 3 through a connector 59. The main body device 3 is connected with the monitor 4 which displays an endoscope image.

Figure 17:
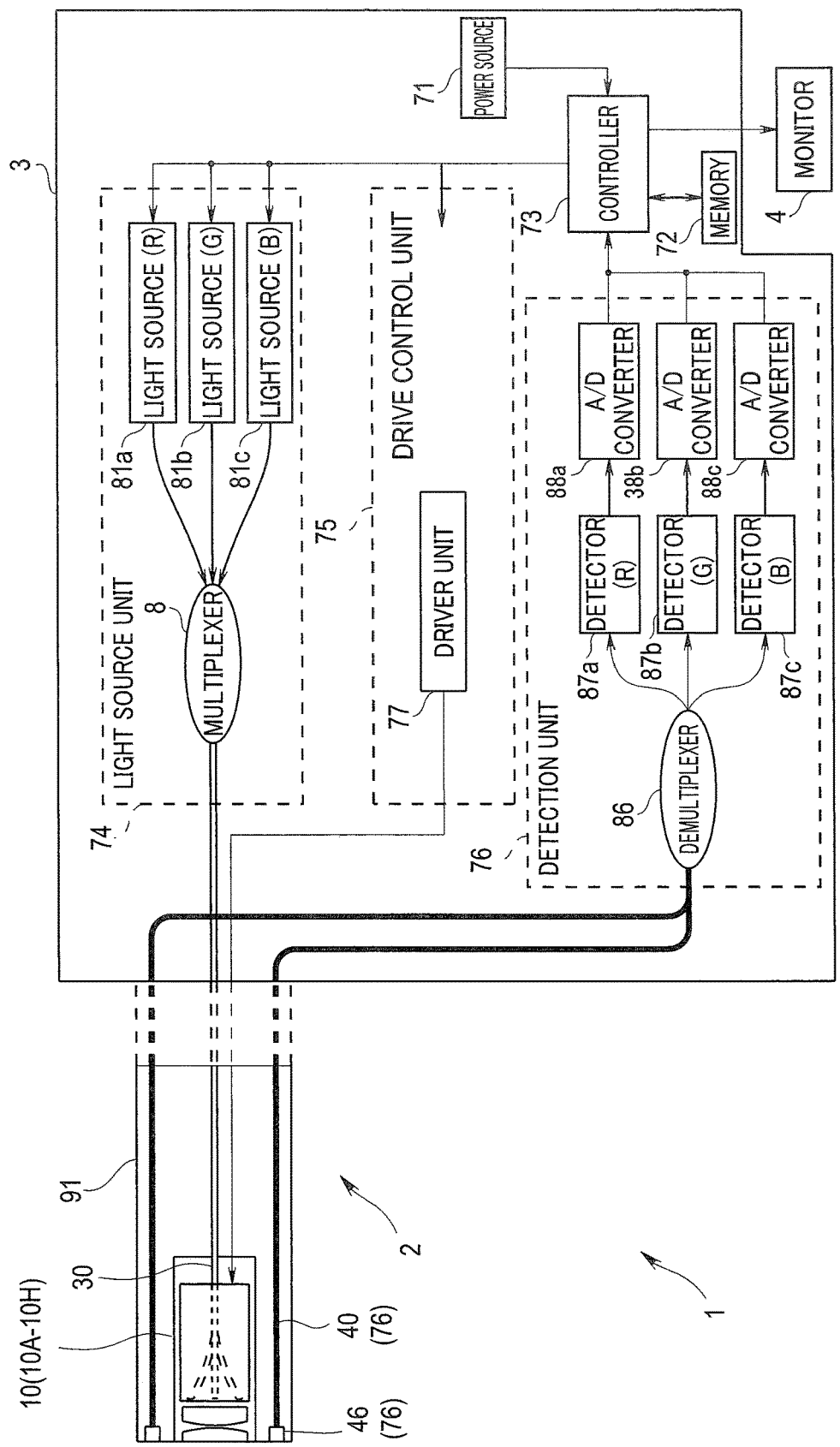
FIG. 17 is a block diagram of the endoscope system including the endoscope in the second embodiment.

Next, the configuration of the endoscope system 1 is illustrated in FIG. 17.

In the inside of the insertion portion 91 of the endoscope 2, the detection fiber 40 which is inserted from a proximal end side to the distal end side along an inner periphery of the insertion portion 91 and guides the reflected light from the subject is provided. To the incidence portion 16 which is a distal end of the detection fiber 40, the detection optical system 46 is disposed. When the endoscope connector 59 of the endoscope 2 is connected to the main body device 3, the detection fiber 40 is connected to a demultiplexer 86.

The main body device 3 is provided with a power source 71, a memory 72, a controller 73, a light source unit 74, a drive control unit 75, and the detection unit 76. The light source unit 74 is provided with three light sources 81a, 81b and 81c, and a multiplexer 82.

The drive control unit 75 is provided with a driver unit 77, and the optical fiber scanning apparatus 10 is driven by the driver unit 77.

The power source 71 supplies power to the controller 73 or the like. In the memory 72, a control program for controlling the entire main body device 3 or the like is stored.

The controller 73 reads the control program from the memory 72, and controls the light source unit 74 and the drive control unit 75. In addition, the controller 73 performs control of performing data processing to light intensity signals of the reflected light from the object detected by the detection unit 76 and displaying the image on the monitor 4.

The light sources 81a, 81b and 81c of the light source unit 74 emit the light of respectively different wavelength bands, the light of the wavelength bands of R (red), G (green) and B (blue) for example, to the multiplexer 82, based on the control of the controller 73. The multiplexer 82 multiplexes the light of the wavelength bands of R, G and B, and emits it to the optical fiber 30.

The driver unit 77 of the drive control unit 75 outputs drive signals for causing the distal end of the optical fiber 30 of the optical fiber scanning apparatus 10 to perform scanning by a desired scanning method to the magnetic field generation unit 21U, based on the control of the controller 73. That is, the driver unit 77 outputs predetermined drive signals to the optical fiber scanning apparatus 10 so as to drive the distal end of the optical fiber 30 in a horizontal direction (X axis direction) and a vertical direction (Y axis direction) regarding an insertion axis (Z axis) of the insertion portion 91.

The detection fiber 40 receives the reflected light reflected on a surface of the subject, and guides the received reflected light to the demultiplexer 86. The demultiplexer 86 is a dichroic mirror or the like for example, and demultiplexes the reflected light by each predetermined wavelength band. Specifically, the demultiplexer 86 demultiplexes the reflected light guided by the detection fiber 40 into the reflected light of the wavelength bands of R, G and B, and outputs the respective reflected light to detectors 87a, 87b and 87c.

The detectors 87a, 87b and 87c are PD elements which detect light intensity of the reflected light of the wavelength bands of R, G and B respectively or the like. Signals of the light intensity detected in the detectors 87a, 87b and 87c are respectively outputted to A/D converters 88a, 88b and 88c. The A/D converters 88a to 88c respectively convert the signals of the light intensity outputted from the detectors 87a to 87c from analog signals to digital signals, and output the digital signals to the controller 73.

The controller 73 generates the object image by executing predetermined image processing to the digital signals from the A/D converters 88a to 88c, and displays the object image on the monitor 4.

Note that monochromatic light may be used or a laser beam may be used as the illumination light.

Since the optical scanning type endoscope 2 has one of the optical fiber scanning apparatuses 10 and 10A to 10H small in the diameter at the distal end portion 94 of the insertion portion 91, the distal end portion is small in the diameter and is lowly invasive. In addition, since the optical fiber scanning apparatuses 10 and 10A to 10H perform highly accurate scan irradiation, the optical scanning type endoscope 2 can obtain excellent images.

The present invention is not limited to the individual embodiments described above, and various modifications, combinations and applications are of course possible without deviating from the scope of the invention.

What is claimed is:

1. An optical fiber scanning apparatus comprising:
a frame body defining a cavity, the cavity having a square cross section;
an optical fiber configured to emit illumination light from a distal end, the distal end of the optical fiber being disposed in the cavity;
a permanent magnet disposed on a portion of the optical fiber arranged in the cavity; and
a magnetic field generator disposed on the frame body, the magnetic field generator comprising a first planar coil, a second planar coil, a third planar coil and a fourth planar coil,
wherein the frame body comprises:
a first frame body having a single piece construction, the first and second planar coils being disposed on respective first and second surfaces of the first frame body, the first and second surfaces forming a first corner such that the first and second surfaces are orthogonal to each other; and
a second frame body having a single piece construction, the third and fourth planar coils being disposed on respective third and fourth surfaces of the second frame body, the third and fourth surfaces forming a second corner such that the third and fourth surfaces are orthogonal to each other;
wherein the first frame body being fixed to the second frame body such that the first and second corners define the square cross section of the cavity; and
the first planar coil fixed to the first surface and the second planar coil fixed to the second surface are both disposed on a base body formed of one sheet of flexible resin.

2. The optical fiber scanning apparatus according to claim 1, wherein the first frame body and the second frame body have a same shape.

3. The optical fiber scanning apparatus according to claim 1, wherein an outer surface of the frame body has a circular cross section and the cavity is provided inside the frame body.

4. The optical fiber scanning apparatus according to claim 1, wherein the first frame body and the second frame body further comprise a positioning portion to provide a positional relation during fixation of the first frame body to the second frame body.

5. The optical fiber scanning apparatus according to claim 4, wherein the positioning portion comprises the first frame body having one of projection or concavity and the second frame body having an other of the projection or concavity, the projection and concavity mating with each other to provide the positional relation during fixation of the first frame body to the second frame body.

6. The optical fiber scanning apparatus according to claim 4, wherein the positioning portion comprises a plurality of contact surfaces.

7. The optical fiber scanning apparatus according to claim 1, further comprising an adjustment portion configured to adjust a positional relation between the first frame body and the second frame body.

8. The optical fiber scanning apparatus according to claim 1, further comprising an optical fiber holding member having a through-hole, the optical fiber being inserted into the through-hole and fixed in the through-hole, the optical fiber holding member being fitted to a rear end portion of the cavity of the frame body.

9. The optical fiber scanning apparatus according to claim 1, further comprising an incidence portion of a detection unit configured to detect reflected light of light with which an object is irradiated from the optical fiber, the incidence portion being arranged in the frame body.

10. The optical fiber scanning apparatus according to claim 9, wherein the incidence portion comprises a distal end of an optical fiber bundle that guides the reflected light.

11. An optical scanning type endoscope comprising:
an insertion portion having a distal end; and
the optical fiber scanning apparatus according to claim 1 disposed at the distal end of the insertion portion.

* * * * *